US00PP36767P2

(12) United States Plant Patent
Guerrero

(10) Patent No.: US PP36,767 P2
(45) Date of Patent: Jun. 24, 2025

(54) ***GYPSOPHILA* PLANT NAMED 'ESM G052'**

(50) Latin Name: *Gypsophila hybrida*
Varietal Denomination: ESM G052

(71) Applicant: GENVIV HOLDINGS, LLC, Miami, FL (US)

(72) Inventor: Maria Elena Guerrero, Quito (EC)

(73) Assignee: GENVIV HOLDING, LLC, Miami, FL (US)

( * ) Notice: Subject to any disclaimer, the term of this patent is extended or adjusted under 35 U.S.C. 154(b) by 0 days.

(21) Appl. No.: 18/981,530

(22) Filed: Dec. 14, 2024

(51) Int. Cl.
*A01H 5/02* (2018.01)
*A01H 6/30* (2018.01)

(52) U.S. Cl.
USPC ..... Plt./354
CPC ..... *A01H 6/30* (2018.05)

(58) Field of Classification Search
USPC ..... Plt./354
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Gypsophila* plant named 'ESM G052', characterized by its strong flowering stems; uniform and freely flowering habit; large and dense inflorescences with large double white-colored flowers; and good postproduction longevity.

1 Drawing Sheet

Botanical designation: *Gypsophila hybrida.*
Cultivar denomination: 'ESM G052'.

CROSS-REFERENCED TO CLOSELY-RELATED APPLICATIONS

A U.S. Plant patent application, Ser. No. 18/981,531, for the *Gypsophila* Plant Named 'ESM G057' was filed by the Inventor, Maria Elena Guerrero concurrently with the instant application on Dec. 14, 2024.

A European Community Plant Breeder's Rights application for the instant plant was filed by the Applicant/Assignee, Genviv Holdings, LLC of Miami, Florida on Sep. 29, 2023, application number 2023/2059 and published on Dec. 15, 2023. Foreign priority is not claimed to this application.

A Colombia Plant Breeder's Rights application for the instant plant was filed by the Applicant/Assignee, Genviv Holdings, LLC of Miami, Florida on Nov. 18, 2024, application number A243197. Foreign priority is not claimed to this application.

BACKGROUND OF THE INVENTION

The present invention relates to a new and distinct cultivar of *Gypsophila* plant, botanically known as *Gypsophila hybrida*, grown commercially as a cut flower, and hereinafter referred to by the name 'ESM G052'.

The new *Gypsophila* plant is a product of a planned breeding program conducted by the Inventor in El Quinche, Pichincha, Ecuador. The objective of the breeding program is to create new productive and uniform *Gypsophila* plants with numerous large double flowers and good postproduction longevity.

The new *Gypsophila* plant originated from a cross-pollination conducted by the Inventor in El Quinche, Pichincha, Ecuador in November 2010 of a proprietary selection of *Gypsophila hybrida* identified as line 251, not patented, as the female, or seed, parent with a proprietary selection of

*Gypsophila hybrida* identified as line 210, not patented, as the male, or pollen, parent. The new *Gypsophila* plant was discovered and selected by the Inventor as a single flowering plant from within the progeny of the stated cross-pollination in a controlled environment in El Quinche, Pichincha, Ecuador in February 2016.

Asexual reproduction of the new *Gypsophila* plant by cuttings in a controlled environment in El Quinche, Pichincha, Ecuador since June 2017 has shown that the unique features of this new *Gypsophila* plant are stable and reproduced true to type in successive generations.

SUMMARY OF THE INVENTION

Plants of the new *Gypsophila* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'ESM G052'. These characteristics in combination distinguish 'ESM G052' as a new and distinct *Gypsophila* plant:

1. Strong flowering stems.
2. Uniform and freely flowering habit.
3. Large and dense inflorescences with large double white-colored flowers.
4. Good postproduction longevity.

In side-by-side comparisons, plants of the new *Gypsophila* differ from plants of the female parent selection in the following characteristics:

1. Plants of the new *Gypsophila* have larger flowers with more petals and petaloids than plants of the female parent selection.
2. Flowers of plants of the new *Gypsophila* are double-types whereas flowers of plants of the female parent selection are semi-double-types.

In side-by-side comparisons, plants of the new *Gypsophila* differ from plants of the male parent selection in the following characteristics:

1. Plants of the new *Gypsophila* are more vigorous and denser than plants of the male parent selection.
2. Stems and flowering stems of plants of the new *Gypsophila* are sturdier than and not as flexible as stems and flowering stems of the male parent selection.
3. Plants of the new *Gypsophila* flower about three to five weeks earlier than plants of the male parent selection.
4. Flowers of plants of the new *Gypsophila* are double-types whereas flowers of plants of the male parent selection are semi-double-types.

Plants of the new *Gypsophila* can also be compared to plants of *Gypsophila hybrida* 'Esm Alicia', disclosed in U.S. Plant Pat. No. 19,479. In side-by-side comparisons, plants of the new *Gypsophila* differ from plants of 'Esm Alicia' in the following characteristics:

1. Plants of the new *Gypsophila* flower three weeks later than plants of 'Esm Alicia'.
2. Flowers of plants of the new *Gypsophila* are double-types whereas flowers of plants of 'Esm Alicia' are semi-double- types.
3. Flowers of plants of the new *Gypsophila* have more petals and petaloids than flowers of plants of 'Esm Alicia'.

Plants of the new *Gypsophila* can also be compared to plants of *Gypsophila hybrida* 'ESM G057', disclosed in U.S. Plant patent application Ser. No. 18/981,531 filed concurrently. In side-by-side comparisons, plants of the new *Gypsophila* differ from plants of 'ESM G057' in the following characteristics:

1. Plants of the new *Gypsophila* are more vigorous than plants of 'ESM G057'.
2. Plants of the new *Gypsophila* flower about one week later than plants of 'ESM G057'.
3. Inflorescences of plants of the new *Gypsophila* have fewer flowers than inflorescences of plants of 'ESM G057'.
4. Flowers of plants of the new *Gypsophila* have fewer petals/petaloids than flowers of plants of 'ESM G057'.
5. Plants of the new *Gypsophila* do not yield as many flowering stems per plant as plants of 'ESM G057'.

BRIEF DESCRIPTION OF THE PHOTOGRAPH

The accompanying photograph illustrates the overall appearance of the new *Gypsophila* plant showing the colors as true as it is reasonably possible to obtain in colored reproductions of this type. Colors in the photograph may differ slightly from the color values cited in the detailed botanical description which accurately describe the colors of the new *Gypsophila* plant.

The photograph is composed of a side perspective view of a typical flowering stem of 'ESM G052' (upper left); close-up view of a typical inflorescence of 'ESM G052' (lower left); close-up view of a typical flower of 'ESM G052' (upper right); and close-up view of upper and lower surfaces of typical leaves of 'ESM G052' (center right).

DETAILED BOTANICAL DESCRIPTION

The aforementioned photograph and following observations and measurements describe plants grown in ground beds in an outdoor nursery in El Quinche, Pichincha, Ecuador in April and under cultural practices which approximate those generally used in commercial cut *Gypsophila* production. During the production of the plants, day temperatures ranged from 14° C. to 21° C., night temperatures ranged from 6° C. to 9° C. and light levels averaged 19.3 klux. Plants were pinched one time three weeks after planting and were 37 weeks old when the photographs and the detailed description were taken. In the following description, color references are made to The Royal Horticultural Society Colour Chart, Sixth Edition, 2015, except where general terms of ordinary dictionary significance are used.

Botanical classification: *Gypsophila hybrida* 'ESM G052'.

Commercial classification: Cut flower *Gypsophila*.

Parentage:

*Female, or seed, parent*.—Proprietary selection of *Gypsophila hybrida* identified as line 251, not patented.

*Male, or pollen, parent*.—Proprietary selection of *Gypsophila hybrida* identified as line 210, not patented.

Propagation:

*Type*.—By vegetative cuttings.

*Time to initiate roots, summer*.—About 15 days at temperatures ranging from 8° C. to 38° C.

*Time to initiate roots, winter*.—About 15 days at temperatures ranging from 14° C. to 28° C.

*Time to produce a rooted young plant, summer*.—About five to six weeks at temperatures ranging from 8° C. to 38° C.

*Time to produce a rooted young plant, winter*.—About five to six weeks at temperatures ranging from 14° C. to 28° C.

*Root description*.—Medium in thickness, fibrous; typically close to 161C in color; actual color of the roots is dependent on substrate composition, water quality, fertilizer, substrate temperature and age of roots.

*Rooting habit*.—Moderately freely branching; medium density.

Plant description:

*Appearance*.—Perennial cut flower; erect and strong flowering stems; inverted triangle form; uniform and freely flowering habit; large double white-colored flowers; vigorous growth habit and moderate growth rate.

*Branching habit*.—About four to seven primary branches each with about six to eight secondary branches developing; about 7.2 flowering stems are typically harvested per year.

*Plant height*.—About 108 cm.

*Plant diameter or spread*.—About 50.1 cm.

*Flowering stems*.—Length: About 94 cm. Diameter: About 4.3 mm. Internode length: About 7.1 cm. Strength: Strong. Texture and luster: Smooth, glabrous; matte. Color, developing: Close to a blend of 144A and 146B. Color, developed: Close to 144A; at the internodes, close to 144B tinged with close to N187A.

Leaf description:

*Arrangement*.—Opposite, decussate, simple; sessile.

*Length*.—About 6.5 cm.

*Width*.—About 1.5 cm.

*Shape*.—Lanceolate.

*Apex*.—Acute.

*Base*.—Cuneate.

*Margin*.—Entire.

*Texture and luster, upper and lower surfaces*.—Smooth, glabrous; matte.

*Venation pattern*.—Parallel.

*Color*.—Developing leaves, upper surface: Close to NN137A to NN137B. Developing leaves, lower surface: Close to NN137B. Fully expanded leaves, upper surface: Close to NN137A; venation, close to NN137A. Fully expanded leaves, lower surface: Close to NN137B; venation, close to 144A.

Flower description:

*Flower arrangement and habit*.—Symmetrical and uniform compound cymes with numerous white-colored flowers, flowers symmetrical, rotate and double; freely flowering habit, about 408 flowers per inflorescence; flowers face mostly upright.

*Flowering response*.—In Ecuador, plants flower year round; early flowering habit; plants begin flowering about 15 weeks after planting.

*Post-production longevity*.—As a cut flower, flowers last for about 13 days; on the plant, flowers last for about 40 days; flowers persistent.

*Fragrance*.—Slightly fragrant; pleasant.

*Inflorescence height*.—About 62.2 cm.

*Inflorescence diameter*.—About 43.3 cm.

*Flower diameter*.—About 1.1 cm.

*Flower depth* (*height*).—About 5.7 mm.

*Flower buds*.—Length: About 2.3 mm. Diameter: About 2.7 mm. Shape: Nearly globose. Texture and luster: Smooth, glabrous; matte. Color: Close to 145D tinged with close to N199A.

*Petals*.—Quantity per flower: About 57 petals/petaloids in about five whorls and fused at the base in clusters. Length: About 5.3 mm. Width: About 2.4 mm. Shape: Spatulate. Apex: Truncate to emarginate. Margin: Entire; slightly undulate. Texture and luster, upper and lower surfaces: Smooth, glabrous; waxy; matte. Color: When opening and fully opening, upper surface: Close to NN155C; venation, close to NN155C; color becoming closer to 155D with subsequent development. When opening and fully opening, lower surface: Close to NN155C; venation, close to NN155C; color becoming closer to 155D with subsequent development.

*Petaloids* (*transformed stamens*).—Length: About 3.9 mm. Width: About 1.6 mm. Shape: Variable, roughly spatulate or lanceolate. Apex: Truncate or emarginate. Margin: Entire; moderately undulate. Texture and luster, upper and lower surfaces: Smooth, glabrous; matte. Color: When opening and fully opening, upper surface: Close to NN155C; venation, close to NN155C; color becoming closer to 155D with subsequent development. When opening and fully opening, lower surface: Close to NN155C; venation, close to NN155C; color becoming closer to 155D with subsequent development.

*Sepals*.—Quantity per flower: About six to eight fused at the base to form a cupped star-shaped calyx. Length: About 3.9 mm. Width: About 1.5 mm. Shape: Lanceolate. Apex: Acute. Margin: Entire. Texture and luster, upper and lower surfaces: Smooth, glabrous; matte. Color: When developing, upper and lower surfaces: Close to NN137A. Fully developed, upper and lower surfaces: Close to 137A.

*Peduncles*.—Length: About 1 cm. Diameter: About 1.4 mm. Strength: Strong. Angle: About 49.4° from lateral branch axis. Texture and luster: Smooth, glabrous; matte. Color: Close to 137B.

*Pedicels*.—Length: About 9.3 mm. Diameter: About 1.4 mm. Strength: Moderately strong. Angle: About 36.3° from peduncle axis Texture and luster: Smooth, glabrous; matte. Color: Close to 144A.

*Reproductive organs*.—Stamens: Quantity per flower: If present, about six to nine. Filament length: About 4.3 mm. Filament color: Close to NN155C. Anther shape: Reniform to globose. Anther length: About 0.7 mm. Anther color: Close to 165D. Pollen amount: None observed. Pistils: Quantity per flower: One. Pistil length: About 7.3 mm. Style length: About 5.4 mm. Style color: Close to NN155C. Stigma shape: Curved apiculate. Stigma diameter: About 0.4 mm to 0.7 mm. Stigma color: Close to NN155C. Ovary color: Close to 144B to 144C. Seeds and fruits: To date, seed and fruit production has not been observed on plants of the new *Gypsophila*.

Pathogen & pest resistance: To date, plants of the new *Gypsophila* have not been observed to be resistant to pathogens and pests common to *Gypsophila* plants.

Temperature tolerance: Flowering plants of the new *Gypsophila* have been observed to tolerate temperatures ranging from about 6° C. to about 28° C.

It is claimed:

1. A new and distinct *Gypsophila* plant named 'ESM G052' as herein illustrated and described.

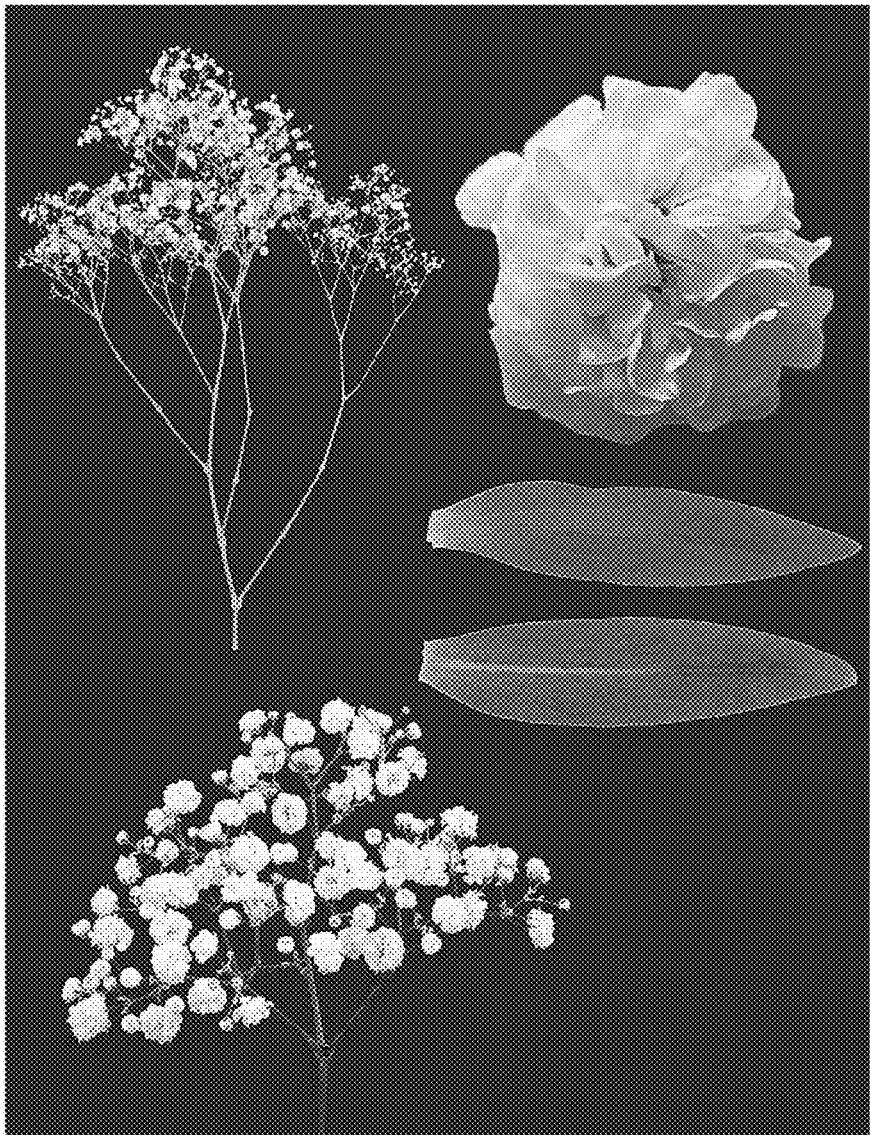

* * * * *